United States Patent
Paulussen et al.

(10) Patent No.: US 11,612,727 B2
(45) Date of Patent: Mar. 28, 2023

(54) VACUUM PATCH

(71) Applicant: KONINKLIJKE PHILIPS N.V., Eindhoven (NL)

(72) Inventors: Igor Wilheimus Franciscus Paulussen, Nuenen (NL); Rick Bezemer, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 66 days.

(21) Appl. No.: 17/055,027

(22) PCT Filed: May 17, 2019

(86) PCT No.: PCT/EP2019/062752
§ 371 (c)(1),
(2) Date: Nov. 12, 2020

(87) PCT Pub. No.: WO2019/219887
PCT Pub. Date: Nov. 21, 2019

(65) Prior Publication Data
US 2021/0220630 A1    Jul. 22, 2021

Related U.S. Application Data

(60) Provisional application No. 62/673,168, filed on May 18, 2018.

(51) Int. Cl.
*A61M 35/00* (2006.01)
*A61B 5/00* (2006.01)

(52) U.S. Cl.
CPC .......... *A61M 35/10* (2019.05); *A61B 5/6834* (2013.01); *A61M 2205/0283* (2013.01); *A61M 2205/33* (2013.01); *A61M 2209/088* (2013.01)

(58) Field of Classification Search
CPC ..... A61B 5/6834; A61B 5/684; A61B 5/6843; A61B 5/6844; A61M 35/10; A61M 2205/0283
See application file for complete search history.

(56) References Cited

U.S. PATENT DOCUMENTS

| | | | | |
|---|---|---|---|---|
| 2007/0270745 | A1* | 11/2007 | Nezhat | A61B 5/6834 604/115 |
| 2008/0078896 | A1* | 4/2008 | Browne | F16B 1/0014 248/205.8 |
| 2010/0228205 | A1* | 9/2010 | Hu | A61M 1/90 604/319 |

(Continued)

FOREIGN PATENT DOCUMENTS

| | | |
|---|---|---|
| CN | 101474432 A | 7/2009 |
| DE | 102008020554 A1 | 10/2008 |
| EP | 2317639 A1 | 5/2011 |

(Continued)

OTHER PUBLICATIONS

International Search Report and Written Opinion, International Application No. PCT/EP2019/062752, dated Aug. 27, 2019.

*Primary Examiner* — Catharine L Anderson
*Assistant Examiner* — Arjuna P Chatrathi (57) ABSTRACT

A medical device (10) configured for attachment to skin of a patient includes a vital sign sensor or drug delivery patch (14); and a plurality of suction cells (12) arranged around a periphery of the vital sign sensor or drug delivery patch.

20 Claims, 5 Drawing Sheets

(56) References Cited

U.S. PATENT DOCUMENTS

2011/0112492 A1   5/2011   Bharti et al.

FOREIGN PATENT DOCUMENTS

| EP | 2395958 B1 | | 12/2017 | | |
|---|---|---|---|---|---|
| EP | 3308695 A1 | | 4/2018 | | |
| GB | 2269012 A | * | 1/1994 | ......... | A61B 5/14542 |
| GB | 2269012 A | | 1/1994 | | |
| WO | 2009141755 A1 | | 11/2009 | | |
| WO | 2010017556 A1 | | 2/2010 | | |
| WO | 2016052818 A1 | | 4/2016 | | |
| WO | WO-2016096391 A | * | 6/2016 | ......... | A61B 5/02427 |
| WO | WO-2016096391 A1 | * | 6/2016 | ......... | A61B 5/02427 |

\* cited by examiner

VACUUM PATCH

This application is the U.S. National Phase application under 35 U.S.C. § 371 of International Application No. PCT/EP2019/062752, filed on 17 May 2019, which claims the benefit of U.S. Provisional Application No. 62/673,168, filed 18 May 2018. These applications are hereby incorporated by reference herein.

FIELD

The following relates generally to the patient sensing arts, wireless patient monitoring arts, wearable patient sensor arts, and related arts.

BACKGROUND

Patient sensing measurement devices, i.e. vital sign sensors, are commonly attached to the skin by an adhesive. Some of these vital sign sensors are wired to a monitoring device, for example as in the case of electrodes for an electrocardiograph (ECG). Some vital sign sensors are self-contained wearable units with on-board signal processing and wireless (e.g. Bluetooth) communication capability. An advantage of these wearable devices is that patient parameters can be measured over a longer period of time.

Another type of medical device is a drug delivery patch, such as a dermal patch that delivers medication into the skin, or a transdermal patch that delivers medication through the skin and into the blood stream.

Such devices need to be attached to the body. Currently this is done with the use of adhesives.

The following discloses new and improved systems and methods for attaching these devices to a patient.

SUMMARY

In one disclosed aspect, a medical device configured for attachment to skin of a patient includes a vital sign sensor or drug delivery patch; and a plurality of suction cells arranged around a periphery of the vital sign sensor or drug delivery patch.

In another disclosed aspect, a medical device configured for attachment to skin of a patient includes a vital sign sensor or drug delivery patch; and a plurality of suction cells arranged around a periphery of the vital sign sensor or drug delivery patch. The suction cells are electrically driven suction cells and comprising an electroactive polymer. A power distribution network includes conductors connected with the suction cells to supply operative electrical power to the plurality of suction cells; and a modulation member configured to control operative electrical power or suction supplied to at least two separate groups of the plurality of suction cells, the at least two separate groups including at least one of the plurality of suction cells.

In another disclosed aspect, a medical device configured for attachment to skin of a patient includes a vital sign sensor or drug delivery patch; and a plurality of suction cells arranged around a periphery of the vital sign sensor or drug delivery patch. The suction cells are electrically driven suction cells. A power distribution network includes a micro-vacuum manifold connected with the suction cells to distribute suction to the plurality of suction cells; and a modulation member configured to control operative electrical power or suction supplied to at least two separate groups of the plurality of suction cells, the at least two separate groups including at least one of the plurality of suction cells.

One advantage resides in providing a sensor or drug delivery patch wearable by a patient without the use of an adhesive.

Another advantage resides in reducing skin irritation resulting from a wearable sensor or drug delivery patch.

Another advantage resides in providing a wearable sensor having vacuum cells with intermittent suction in a planned order to reduce skin irritation.

Another advantage resides in providing one or more of the foregoing advantages in conjunction with continuous monitoring of the attachment.

Another advantage resides in providing a wearable sensor without adhesives to easily position and reposition the sensor.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

As noted previously, devices such as vital sign sensors or drug delivery patches need to be attached to the body. Currently this is done with the use of adhesives. A disadvantage of adhesives is that they can cause skin irritation and damage. Some types of adhesives can also leave residue. Furthermore, an adhered vital sign sensor or drug delivery patch can fall off without any indication being provided that it is no longer attached.

The following discloses a medical patch (e.g., a vital sign sensor to be attached to the skin of a patient, or a drug delivery patch) with a set of suction cells for attachment. The medical patch may be a vital sign sensor, a dermal patch for delivery of medication into the skin, a transdermal patch for delivery of medication through the skin and into the blood stream, or so forth. The suction cells provide an attachment mechanism that is less irritating to the skin as compared with adhesive, and produces less (preferably no) skin damage.

In embodiments disclosed herein, a peripheral ring of suction cells encircle the periphery of the medical patch. The suction cells may be electrically driven suction cells, or may be connected to an external vacuum pump. In the former approach, the suction cell may be an electroactive polymer. In one form factor, the polymer forms a tube that is extended when electrically biased so as to draw vacuum, thereby creating suction on the patient's skin. In another form factor, the polymer tube extends lengthwise to draw vacuum.

In some embodiments the medical patch further includes on-board components for driving the suction cells. In the electrically driven embodiment this can include electrical storage and wiring (e.g. a flexible printed circuit board) for conveying electrical power to the suction cells. In the external vacuum pump embodiment the on-board components include a micro-vacuum manifold for distributing suction provided by the external vacuum pump to the peripheral suction cells.

In embodiments disclosed herein, the suction provided by the suction cells may be modulated. For example, one-half of the suction cells may be "Group A" and the other half "Group B", with suction cells of Groups A and B alternating along the periphery. Groups A and B can be driven using sinusoidal (or sinusoidal-squared) suction with a 180° phase shift between the two groups, leading to a constant average suction over the patch periphery but only half of the suction for any given suction cell. Other modulation schemes are contemplated, e.g. three groups with 120° phase shifts would achieve the same average effect with only one-third of the suction drawn by any individual cell. Modulation schemes with varying average suction could also work, e.g. binary on/off suction at each cell, but the inventors indicated that in any modulation scheme it should be ensured that there is sufficient suction at all times to keep the patch attached.

Such modulation can be implemented by a microprocessor controlling the electrical drive power to the electrically driven suction cells; or, in the external vacuum pump embodiment micro-electromechanical vacuum valves could be used.

In the case of electrically driven suction cells, another advantage of the modulation scheme approach is that the suction is refreshed at each cycle, so as to avoid gradual loss of vacuum (and consequent loss of suction) due to slow leakage.

In embodiments employing an external vacuum pump, a further advantage of the disclosed approach is that airflow on the vacuum line can be used to verify proper attachment of the medical patch. If the patch falls off, airflow will increase, i.e. the vacuum pump will "see" an open flow circuit. Similar on-board monitoring might be possible in the case of electrically driven suction cells, e.g. the impedance seen by the driver circuit could be used to detect loss of attachment. This type of attachment loss detection could be incorporated into an alarm framework in the case of a medical patch with short-range wireless connectivity (e.g. a wireless vital sign sensor patch).

In the case of electrically driven suction cells, operation of the suction attachment can be controlled by an on/off button, or by a sensor that detects patch placement onto the skin. In embodiments driven by an external vacuum pump the operative connection of the patch to the vacuum pump (e.g. by an air hose) may serve as the on/off control, e.g. by detecting the drawing of suction by the pump.

Figure 1:
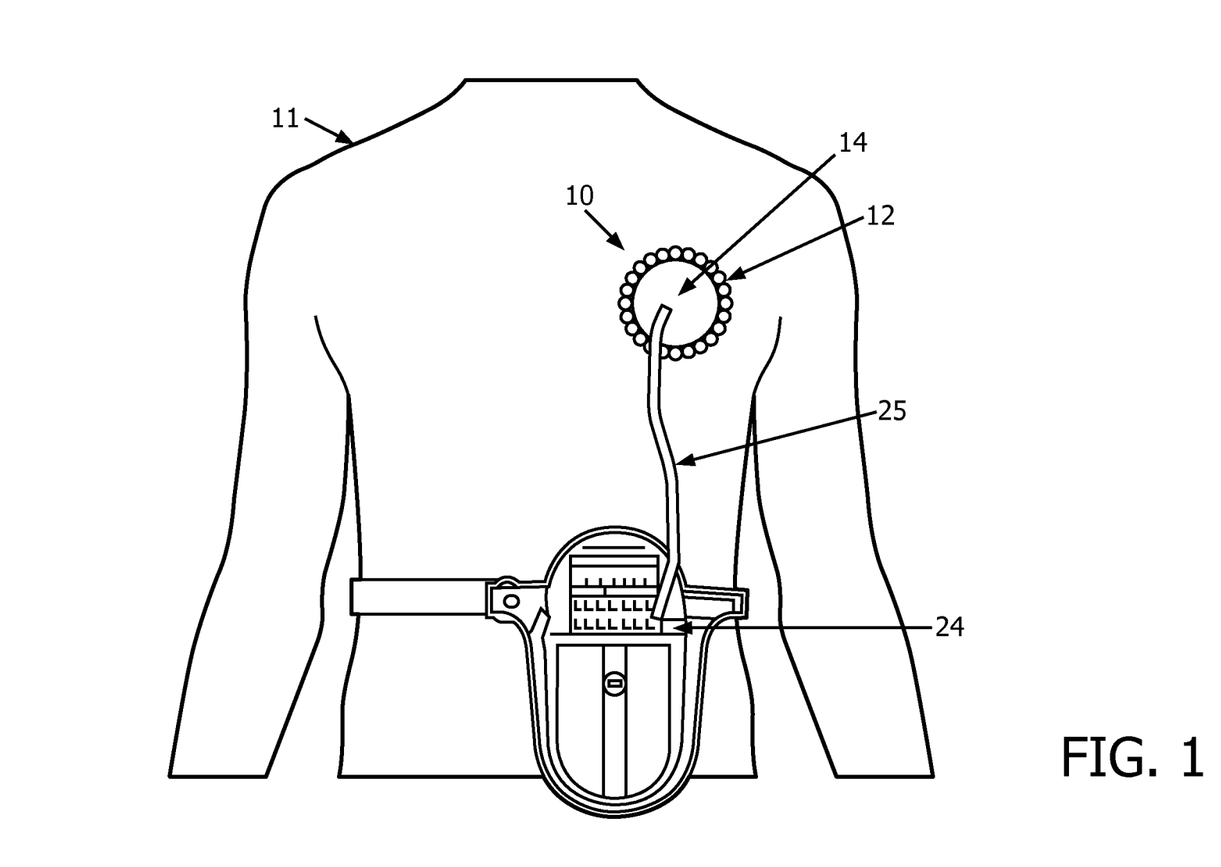
FIG. 1 diagrammatically shows a medical device for attachment a patient according to one aspect.

With reference to FIG. 1, an illustrative medical device 10 configured for attachment to skin of a patient 11 is shown. As shown in FIG. 1, the device 10 includes a plurality of suction cells 12 arranged around a periphery of a vital sign sensor or drug delivery patch 14 (e.g., an electrocardiogram (ECG) electrode, a photoplethysmography (PPG) sensor, an ultrasound sensor, an imaging probe such as an ultrasound probe, and so forth). The vital sign sensor or drug delivery patch 14 is shown as having a circular shape, but more generally can have any other suitable shape (e.g., rectangular, triangular, elliptical, square, and so forth). The device 10 is configured (e.g., sized and shaped) to be attached to skin of the patient 11.

Figure 2:
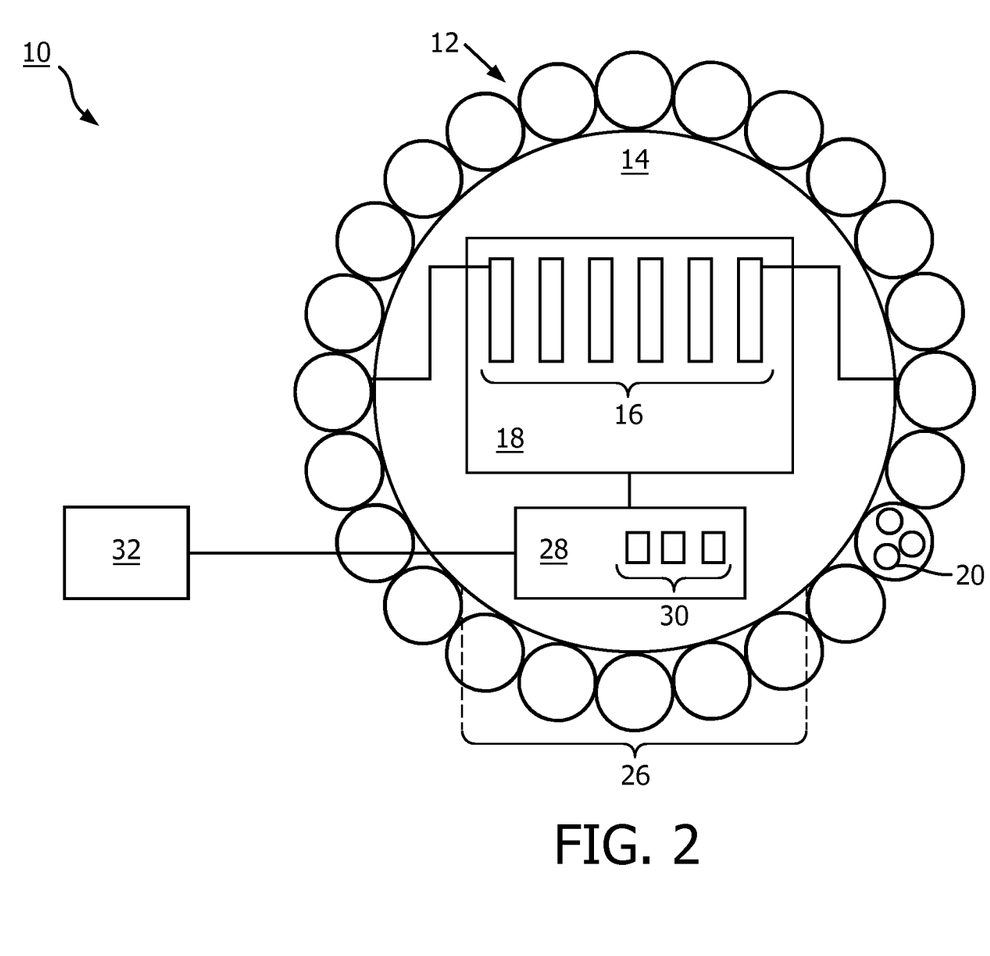
FIG. 2 diagrammatically shows another embodiment of the device of FIG. 1.

With reference to FIG. 2, and with continuing reference to FIG. 1, in some embodiments, the suction cells 12 are electrically driven suction cells. For example, a volume of the suction cells 12 can be increased by apply suction to the suction cells while an amount of air inside of the volume of the suction cells remains constant. To supply operative electrical power to the suction cells 12, the device 10 includes conductors 16 (e.g., electrical conductors) connected with the suction cells. Each suction cell 12 can be connected with a corresponding conductor 16, while in other examples, a single conductor 16 can be configured to supply electrical power to several suction cells (detailed connections not shown in FIG. 2). In some examples, the device 10 further includes a printed circuit board (PCB) 18, and the conductors 16 comprises printed circuitry of the PCB. The PCB 18 can be disposed on a portion of the vital sign sensor or drug delivery patch 14.

Figure 4:
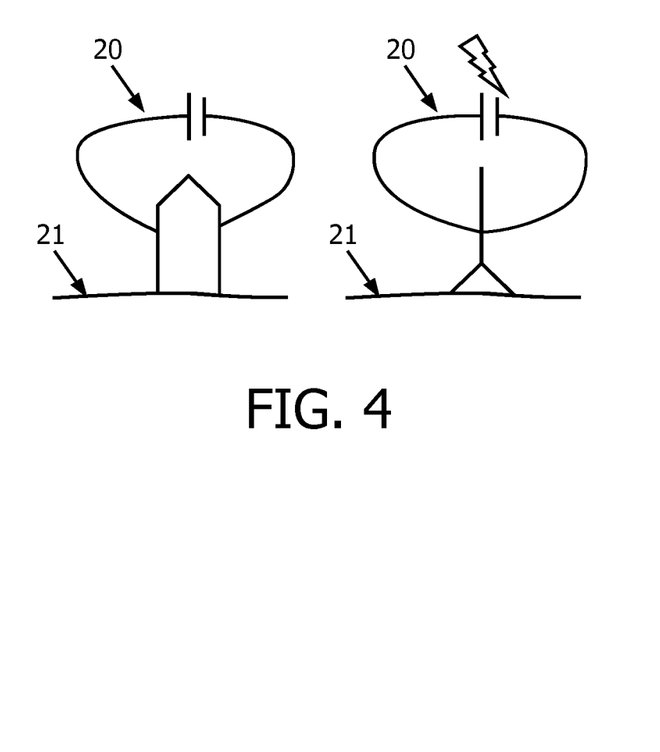
FIGS. 4 and 5 diagrammatically show different embodiments of suction activation of the devices of FIGS. 1-3.
Figure 5:
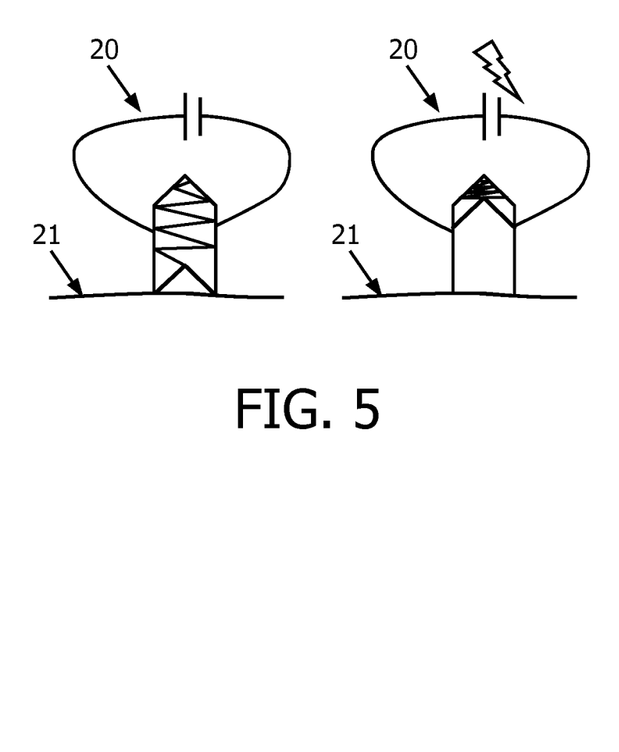

With continuing reference to FIG. 2 and with brief further reference to FIGS. 4 and 5, in some embodiments, the suction cells 12 are electrically driven suction cells that comprise an electroactive polymer. In some examples, the electrically driven suction cells 12 comprise hollow tubes 20 closed at one end. However, the suction cells 12 can comprise any suitable shape (e.g., cubic-shaped, box-shaped, and so forth). In FIG. 2, a plurality of such tubes 20 are illustrated collectively forming one of the suction cells 12, and it is to be understood that each of the other suction cells 12 are similarly constructed. In other embodiments, each suction cell may be formed as a single tube 20. In some examples, as diagrammatically shown in FIG. 4, the tubes 20 of the suction cells 12 are configured to extend when electrically biased by the operative electrical power in order to draw suction against skin 21 to which the suction cell grips. The left-hand diagram of FIG. 4 shows the tube 20 without applied electrical bias. The right-hand diagram of FIG. 4 shows the tube 20 with applied electrical bias. The electrical bias decreases the diameter of the tube 20 and draws air out thereby forming a suction attachment to the skin 21. In other examples, as diagrammatically shown in FIG. 5, the tubes 20 of the suction cells 12 are configured to extend lengthwise when electrically biased by the operative electrical power. The left-hand diagram of FIG. 5 shows the tube 20 without applied electrical bias. The right-hand diagram of FIG. 5 shows the tube 20 with applied electrical bias. The electrical bias lengthens the tube 20 and thereby increases the interior volume of the tube 20, thereby forming a suction attachment to the skin 21.

Figure 3:
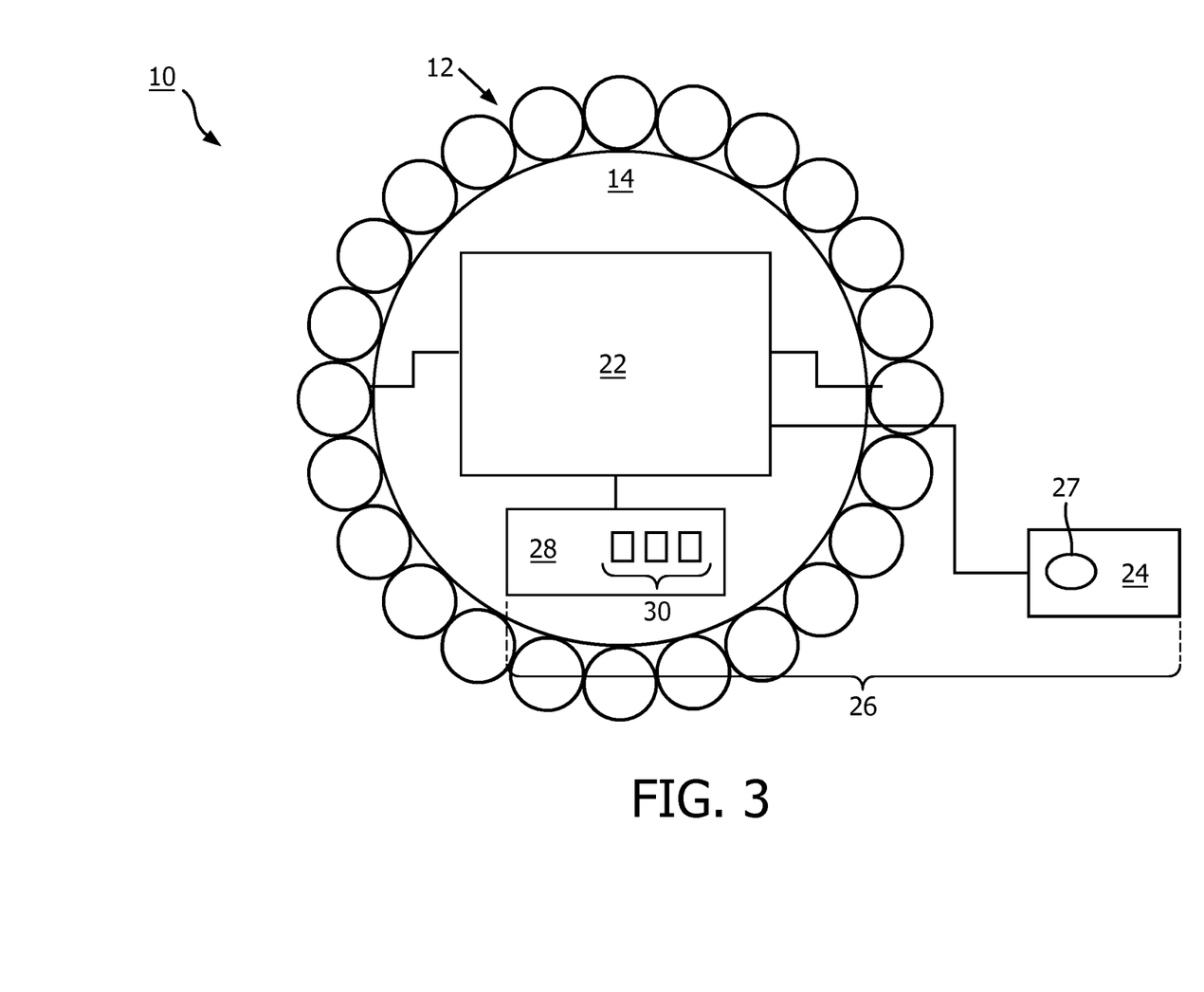
FIG. 3 diagrammatically shows another embodiment of the device of FIG. 1.

In other embodiments, with reference now to FIG. 3 and with continuing reference to FIGS. 1 and 2, the suction cells 12 may be mechanically driven in that an external vacuum is applied to pull the suction. For example, a volume of the suction cells 12 remains constant, while an amount of air inside of the volume of the suction cells is decreased when suction is applied to the suction cells. In the embodiment of FIG. 3, the device 10 includes a micro-vacuum manifold 22 connected with the suction cells 12 to distribute suction to the plurality of suction cells (detailed connections not shown in FIG. 3). The manifold 22 can be disposed on a portion for the vital sign sensor or drug delivery patch 14. An associated vacuum pump 24 (diagrammatically shown in FIG. 3; see also FIG. 1) is connected with the manifold 22 via a vacuum tube 25 (see FIG. 1) to deliver power in the form of vacuum suction to the manifold 22. The vacuum pump 24 can include an on/off switch 27 to control operation of the pump.

In another example, the on/off switch 27 can comprise a foot pedal (not shown) for operation by a medical professional.

Figure 6:
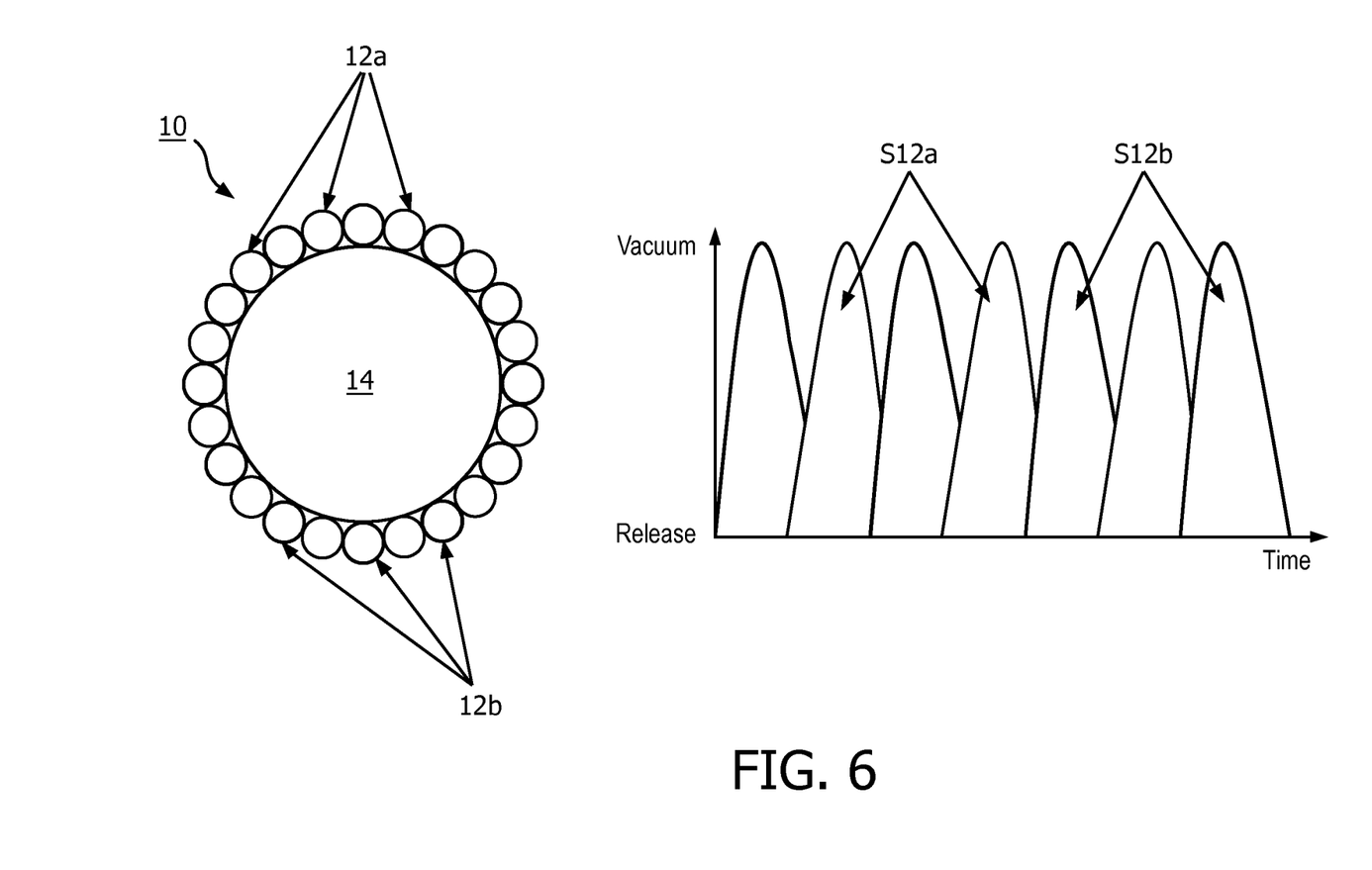
FIG. 6 diagrammatically shows a suction cycle of the devices of FIGS. 1-3.

With reference now to FIG. 6, to avoid skin irritation and or damage, the suction cells 12 can be activated intermittently in a certain order to create the suction. As shown FIG. 6 in the left-hand diagram of the device 10, the suction cells are divided, in this embodiment, into two groups: a first suction cell group 12a, and a second suction cell group 12b. As shown in FIG. 6 in the right-hand plot, the first suction cell group 12a is operated with a first periodic suction-versus time schedule S12a, while the second suction cell group 12b is operated with a second periodic suction-versus time schedule S12b that is of the same shape and magnitude as the first periodic suction-versus time schedule S12a but offset by 180° in phase. As indicated in FIGS. 2 and 3, the device 10 also comprises a power distribution network 26 for implementing the two periodic suction-versus-time schedules. The power distribution network 26 includes either the conductors 16 (electrical suction cells embodiment of FIG. 2) or the manifold 22 (mechanical suction cells embodiment of FIG. 3) to supply suction to the respective suction cell groups 12a, 12b with their respective periodic suction-versus time schedules S12a, S12b. The power distribution network 26 includes a modulation member 28 configured to control operative electrical power or suction supplied to at least two separate groups of the plurality of suction cells 12a, 12b to implement the respective schedules S12a, S12b. Each separate group includes at least one of the plurality of suction cells 12. In the illustrative example of FIG. 6, half of the suction cells 12 are in a first group 12a, and the other half of the suction cells are in a second group 12b, and the cells of the two groups are interleaved as depicted in the left-hand diagram of FIG. 6. The first and second groups of suction cells 12a, 12b are selectively activated intermittently with suction applied to the cells in each respective group according to the respective schedule S12a, S12b. The suction cells of the two groups 12a, 12b are interleaved around the periphery of the vital sign sensor or drug delivery patch 14.

In the example of FIG. 6, referring to the right-hand plot, the total suction provided by all the suction cells 12 is equal to the additive combination of the suction provided by the suction cell group 12a (this is the suction S12a) and the suction provided by the suction cell group 12b (this is the suction S12b). If, for example, the periodic suction-versus-time schedule S12a is a cosine-squared function of the form $A^*\cos^2(wt)$ and the periodic suction-versus-time schedule S12b is a sine-squared function of the form $A^*\sin^2(wt)$, where t denotes time, w denotes an angular frequency, and A denotes amplitude, then the total suction at any given time is thus:

$$A^*\cos^2(wt)+A^*\sin^2(wt)=A[\cos^2(wt)+\sin^2(wt)]=A$$

so that the total suction applied as a function of time is constant. This ensures there are no intermittent losses of total suction, even though the suction applied to individual suction cells does intermittently go to zero. In the example of FIG. 6, right-hand plot, the periodic suction-versus-time schedules S12a, S12b are not precisely sinusoidal-squared functions, but are offset in phase so that the total suction never goes to zero, and more generally should never go to a value low enough to compromise the integrity of the suction seal of the medical device 10 to the skin of the patient.

Thus, the modulation member 28 is configured to alternate supply of the operative electrical power or suction amongst the at least two separate groups of the plurality of suction cells. To do so, the modulation member 28 comprises vacuum valves 30 operable connected with the plurality of suction cells 12. The modulation member 28 is configured to supply operative electrical power or suction to a first group of the at least at least two separate groups of the plurality of suction cells 12 while not supplying operative electrical power or suction to at least a second group at least two separate groups of the plurality of suction cells.

When the suction cells 12 comprise an electroactive polymer, the modulation member 28 includes at least one electronic processor 32 operably connected with the plurality of suction cells and programmed to control the operative electrical power supplied to the at least two separate groups of the plurality of suction cells. When the device 10 includes the micro-vacuum manifold 22, the vacuum pump 24 is configured to control the operative electrical power supplied to the at least two separate groups of the plurality of suction cells.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof

The invention claimed is:

1. A medical device configured for attachment to skin of a patient, the device comprising:
   a vital sign sensor or drug delivery patch; and
   a plurality of suction cells arranged on a periphery of the vital sign sensor or drug delivery patch, wherein the plurality of suction cells surround a circumference of the vital sign sensor or drug delivery patch.

2. The medical device of claim 1, wherein the suction cells are electrically driven suction cells, the medical device further comprising conductors connected with the suction cells to supply operative electrical power to the plurality of suction cells.

3. The medical device of claim 2, wherein the electrically driven suction cells comprise an electroactive polymer.

4. The medical device of claim 3, wherein the electrically driven suction cells comprise hollow tubes closed at one end and configured to extend lengthwise when electrically biased by the operative electrical power.

5. The medical device of 2, further comprising:
   a printed circuit board, the conductors comprising printed circuitry of the printed circuit board.

6. The medical device of claim 1, further comprising a micro-vacuum manifold connected with the suction cells to distribute suction to the plurality of suction cells.

7. The medical device of claim 6, further comprising a vacuum pump connected with the micro-vacuum manifold.

8. The medical device of claim 1, further comprising:
   a power distribution network including:
      one of (i) conductors connected with the suction cells to supply operative electrical power to the plurality of suction cells or (ii) a micro-vacuum manifold connected with the suction cells to distribute suction to the plurality of suction cells; and
   a modulation member configured to control operative electrical power or suction supplied to at least two separate groups of the plurality of suction cells, the at least two separate groups including at least one of the plurality of suction cells.

9. The medical device of claim 8, wherein the modulation member is configured to supply operative electrical power or suction to a first group of the at least two separate groups of the plurality of suction cells while not supplying operative electrical power or suction to at least a second group of the at least two separate groups of the plurality of suction cells.

10. The medical device of claim 8, wherein the suction cells comprise an electroactive polymer, and the modulation member comprises at least one electronic processor operably connected with the plurality of suction cells and programmed to control the operative electrical power supplied to the at least two separate groups of the plurality of suction cells.

11. The medical device of claim 8, wherein the modulation member comprises vacuum valves operably connected with the plurality of suction cells.

12. The medical device of claim 8, wherein the modulation member is configured to alternate supply of the operative electrical power or suction amongst the at least two separate groups of the plurality of suction cells.

13. The medical device of claim 12, wherein the suction cells of the at least two separate groups of the plurality of suction cells are interleaved around the periphery of the vital sign sensor or drug delivery patch.

14. A medical device configured for attachment to skin of a patient, the device comprising:
   a vital sign sensor or drug delivery patch; and
   a plurality of suction cells arranged on a periphery of the vital sign sensor or drug delivery patch, the suction cells being electrically driven suction cells and comprising an electroactive polymer, wherein the plurality of suction cells surround a circumference of the vital sign sensor or drug delivery patch;
   a power distribution network including:
      conductors connected with the suction cells to supply operative electrical power to the plurality of suction cells; and
      a modulation member configured to control operative electrical power or suction supplied to at least two separate groups of the plurality of suction cells, the at least two separate groups including at least one of the plurality of suction cells.

15. The medical device of claim 14, wherein the electrically driven suction cells comprise hollow tubes closed at one end and configured to extend lengthwise when electrically biased by the operative electrical power.

16. The medical device of claim 14, wherein the modulation member is configured to supply operative electrical power or suction to a first group of the at least two separate groups of the plurality of suction cells while not supplying operative electrical power or suction to at least a second group of the at least two separate groups of the plurality of suction cells;
   wherein the modulation member comprises at least one electronic processor operably connected with the plurality of suction cells and programmed to control the operative electrical power supplied to the at least two separate groups of the plurality of suction cells.

17. A medical device configured for attachment to skin of a patient, the device comprising:
   a vital sign sensor or drug delivery patch; and
   a plurality of suction cells arranged on a periphery of the vital sign sensor or drug delivery patch, the suction cells being electrically driven suction cells, wherein the plurality of suction cells surround a circumference of the vital sign sensor or drug delivery patch;
   a power distribution network including:
      a micro-vacuum manifold connected with the suction cells to distribute suction to the plurality of suction cells; and
      a modulation member configured to control operative electrical power or suction supplied to at least two separate groups of the plurality of suction cells, the at least two separate groups including at least one of the plurality of suction cells.

18. The medical device of claim 17, further comprising a vacuum pump connected with the micro-vacuum manifold.

19. The medical device of claim 17, wherein the modulation member comprises vacuum valves operably connected with the plurality of suction cells.

20. The medical device of claim 17, wherein the suction cells of the at least two separate groups of the plurality of suction cells are interleaved around the periphery of the vital sign sensor or drug delivery patch.

\* \* \* \* \*